(12) United States Patent
Bayer et al.

(10) Patent No.: US 8,197,399 B2
(45) Date of Patent: Jun. 12, 2012

(54) SYSTEM AND METHOD FOR PRODUCING AND IMPROVING IMAGES

(75) Inventors: Lex Bayer, Palo Alto, CA (US); Michael Stewart, Menlo Park, CA (US)

(73) Assignee: Avantis Medical Systems, Inc., Sunnyvale, CA (US)

( * ) Notice: Subject to any disclaimer, the term of this patent is extended or adjusted under 35 U.S.C. 154(b) by 1328 days.

(21) Appl. No.: 11/751,596

(22) Filed: May 21, 2007

(65) Prior Publication Data

US 2007/0270642 A1    Nov. 22, 2007

Related U.S. Application Data

(60) Provisional application No. 60/801,748, filed on May 19, 2006.

(51) Int. Cl.
- *A61B 1/00* (2006.01)
- *A61B 1/04* (2006.01)
- *H04N 7/18* (2006.01)

(52) U.S. Cl. .......................................... 600/113; 348/72

(58) Field of Classification Search .......... 382/167–169, 382/172, 270–271, 273–274; 600/101, 109, 600/113, 160, 103–104; 348/71, 72
See application file for complete search history.

(56) References Cited

U.S. PATENT DOCUMENTS

| | | |
|---|---|---|
| 3,437,747 A | 4/1969 | Sheldon |
| 3,610,231 A | 10/1971 | Takahashi et al. |
| 3,643,653 A | 2/1972 | Takahashi et al. |
| 3,739,770 A | 6/1973 | Mori |
| 3,889,662 A | 6/1975 | Mitsui |
| 3,897,775 A | 8/1975 | Furihata |
| 3,918,438 A | 11/1975 | Hayamizu et al. |
| 4,261,344 A | 4/1981 | Moore et al. |
| 4,351,587 A | 9/1982 | Matsuo et al. |
| 4,398,811 A | 8/1983 | Nishioka et al. |
| 4,494,549 A | 1/1985 | Namba et al. |
| 4,573,450 A | 3/1986 | Arakawa |
| 4,586,491 A | 5/1986 | Carpenter |
| 4,625,236 A | 11/1986 | Fujimori et al. |
| 4,646,722 A | 3/1987 | Silverstein et al. |

(Continued)

FOREIGN PATENT DOCUMENTS

CN    1 628 603    6/2005

(Continued)

OTHER PUBLICATIONS

U.S. Appl. No. 11/828,835, filed Jun. 14, 2005, Bayer.

(Continued)

*Primary Examiner* — Philip R Smith
(74) *Attorney, Agent, or Firm* — Morrison & Foerster LLP (57) ABSTRACT

A method for displaying images includes adjusting at least one characteristic of an image from a first imaging device of an endoscope to match at least one corresponding characteristic of an image from a second imaging device of the endoscope. The at least one characteristic may be one or more of color, contrast and brightness. An endoscopic system includes an endoscope including a first imaging device and a second imaging device, and a display device that displays an image from the first imaging device of the endoscope and an image from the second imaging device of the endoscope, wherein the images are sized so that an object, when placed at the same distance from the imaging devices, appears to have about the same size in the images.

23 Claims, 6 Drawing Sheets

U.S. PATENT DOCUMENTS

| | | |
|---|---|---|
| 4,699,463 A | 10/1987 | D'Amelio et al. |
| 4,721,097 A | 1/1988 | D'Amelio |
| 4,727,859 A | 3/1988 | Lia |
| 4,741,326 A | 5/1988 | Sidall et al. |
| 4,790,295 A | 12/1988 | Tashiro |
| 4,800,870 A | 1/1989 | Reid, Jr. |
| 4,825,850 A | 5/1989 | Opie et al. |
| 4,836,211 A | 6/1989 | Sekino et al. |
| 4,846,154 A | 7/1989 | MacAnally et al. |
| 4,852,551 A | 8/1989 | Opie et al. |
| 4,853,773 A | 8/1989 | Hibino et al. |
| 4,862,873 A | 9/1989 | Yajima et al. |
| 4,867,138 A | 9/1989 | Kubota et al. |
| 4,869,238 A | 9/1989 | Opie et al. |
| 4,870,488 A | 9/1989 | Ikuno et al. |
| 4,873,572 A | 10/1989 | Miyazaki et al. |
| 4,873,965 A | 10/1989 | Danieli |
| 4,884,133 A | 11/1989 | Kanno et al. |
| 4,899,732 A | 2/1990 | Cohen |
| 4,905,667 A | 3/1990 | Foerster et al. |
| 4,907,395 A | 3/1990 | Opie et al. |
| 4,911,148 A | 3/1990 | Sosnowski et al. |
| 4,911,564 A | 3/1990 | Baker |
| 4,926,258 A | 5/1990 | Sasaki |
| 4,947,827 A | 8/1990 | Opie et al. |
| 4,947,828 A | 8/1990 | Carpenter et al. |
| 4,979,496 A | 12/1990 | Komi |
| 4,991,565 A | 2/1991 | Takahashi et al. |
| 5,019,040 A | 5/1991 | Itaoka et al. |
| 5,025,778 A | 6/1991 | Silverstein et al. |
| 5,026,377 A | 6/1991 | Burton et al. |
| 5,050,585 A | 9/1991 | Takahashi |
| RE34,100 E | 10/1992 | Opie et al. |
| RE34,110 E | 10/1992 | Opie et al. |
| 5,159,446 A | 10/1992 | Hibino et al. |
| 5,166,787 A | 11/1992 | Irion |
| 5,178,130 A | 1/1993 | Kaiya et al. |
| 5,187,572 A | 2/1993 | Nakamura et al. |
| 5,193,525 A | 3/1993 | Silverstein et al. |
| 5,196,928 A | 3/1993 | Karasawa et al. |
| 5,253,638 A | 10/1993 | Tamburrino et al. |
| 5,260,780 A | 11/1993 | Staudt, III |
| 5,271,381 A | 12/1993 | Ailinger et al. |
| 5,305,121 A | 4/1994 | Moll |
| 5,318,031 A | 6/1994 | Mountford et al. |
| 5,329,887 A | 7/1994 | Ailinger et al. |
| 5,337,734 A | 8/1994 | Saab |
| 5,381,784 A | 1/1995 | Adair |
| 5,398,685 A | 3/1995 | Wilk et al. |
| 5,406,938 A | 4/1995 | Mersch et al. |
| 5,434,669 A | 7/1995 | Tabata et al. |
| 5,443,781 A | 8/1995 | Saab |
| 5,447,148 A | 9/1995 | Oneda et al. |
| 5,483,951 A | 1/1996 | Frassica et al. |
| 5,494,483 A | 2/1996 | Adair |
| 5,518,501 A | 5/1996 | Oneda et al. |
| 5,520,607 A | 5/1996 | Frassica et al. |
| 5,530,238 A | 6/1996 | Meulenbrugge et al. |
| 5,533,496 A | 7/1996 | De Faria-Correa et al. |
| 5,536,236 A | 7/1996 | Yabe et al. |
| 5,556,367 A | 9/1996 | Yabe et al. |
| 5,613,936 A | 3/1997 | Czarnek et al. |
| 5,614,943 A | 3/1997 | Nakamura et al. |
| 5,626,553 A | 5/1997 | Frassica et al. |
| 5,634,466 A | 6/1997 | Gruner |
| 5,653,677 A | 8/1997 | Okada et al. |
| 5,667,476 A | 9/1997 | Frassica et al. |
| 5,679,216 A | 10/1997 | Takayama et al. |
| 5,681,260 A | 10/1997 | Ueda et al. |
| 5,682,199 A | 10/1997 | Lankford |
| 5,685,822 A | 11/1997 | Harhen |
| 5,692,729 A | 12/1997 | Harhen |
| 5,696,850 A | 12/1997 | Parulski et al. |
| 5,702,348 A | 12/1997 | Harhen |
| 5,706,128 A | 1/1998 | Greenberg |
| 5,711,299 A | 1/1998 | Manwaring et al. |
| 5,722,933 A | 3/1998 | Yabe et al. |
| 5,752,912 A | 5/1998 | Takahashi et al. |
| 5,762,603 A | 6/1998 | Thompson |
| 5,817,061 A | 10/1998 | Goodwin et al. |
| 5,827,177 A | 10/1998 | Oneda et al. |
| 5,833,603 A | 11/1998 | Kovacs et al. |
| 5,843,103 A | 12/1998 | Wulfman |
| 5,843,460 A | 12/1998 | Labigne et al. |
| 5,860,914 A | 1/1999 | Chiba et al. |
| 5,876,329 A | 3/1999 | Harhen |
| 5,916,147 A | 6/1999 | Boury |
| 5,924,977 A | 7/1999 | Yabe et al. |
| 5,938,587 A | 8/1999 | Taylor et al. |
| 5,982,932 A | 11/1999 | Prokoski |
| 5,989,182 A | 11/1999 | Hori et al. |
| 5,989,224 A | 11/1999 | Exline et al. |
| 6,017,358 A | 1/2000 | Yoon |
| 6,026,323 A | 2/2000 | Skladnev et al. |
| 6,066,090 A | 5/2000 | Yoon |
| 6,099,464 A | 8/2000 | Shimizu et al. |
| 6,099,466 A | 8/2000 | Sano et al. |
| 6,099,485 A | 8/2000 | Patterson |
| 6,106,463 A | 8/2000 | Wilk |
| 6,174,280 B1 | 1/2001 | Oneda et al. |
| 6,190,330 B1 | 2/2001 | Harhen |
| 6,214,028 B1 | 4/2001 | Yoon et al. |
| 6,261,226 B1 | 7/2001 | McKenna et al. |
| 6,261,307 B1 | 7/2001 | Yoon et al. |
| 6,277,064 B1 | 8/2001 | Yoon |
| 6,296,608 B1 | 10/2001 | Daniels et al. |
| 6,301,047 B1 | 10/2001 | Hoshino et al. |
| 6,350,231 B1 | 2/2002 | Ailinger et al. |
| 6,369,855 B1 | 4/2002 | Chauvel et al. |
| 6,375,653 B1 | 4/2002 | Desai |
| 6,387,043 B1 | 5/2002 | Yoon |
| 6,433,492 B1 | 8/2002 | Buonavita |
| 6,456,684 B1 | 9/2002 | Mun et al. |
| 6,461,294 B1 | 10/2002 | Oneda et al. |
| 6,482,149 B1 | 11/2002 | Torii |
| 6,527,704 B1 | 3/2003 | Chang et al. |
| 6,547,724 B1 | 4/2003 | Soble et al. |
| 6,554,767 B2 | 4/2003 | Tanaka |
| 6,564,088 B1 | 5/2003 | Soller et al. |
| 6,640,017 B1 | 10/2003 | Tsai et al. |
| 6,648,816 B2 | 11/2003 | Irion et al. |
| 6,683,716 B1 | 1/2004 | Costales |
| 6,687,010 B1 | 2/2004 | Horii et al. |
| 6,697,536 B1 | 2/2004 | Yamada |
| 6,699,180 B2 | 3/2004 | Kobayashi |
| 6,736,773 B2 * | 5/2004 | Wendlandt et al. ........... 600/173 |
| 6,748,975 B2 | 6/2004 | Hartshorne et al. |
| 6,796,939 B1 | 9/2004 | Konomura et al. |
| 6,833,871 B1 | 12/2004 | Merrill et al. |
| 6,845,190 B1 | 1/2005 | Smithwick et al. |
| 6,891,977 B2 | 5/2005 | Gallagher |
| 6,916,286 B2 | 7/2005 | Kazakevich |
| 6,928,314 B1 | 8/2005 | Johnson et al. |
| 6,929,636 B1 | 8/2005 | von Alten |
| 6,947,784 B2 | 9/2005 | Zalis |
| 6,951,536 B2 | 10/2005 | Yokoi et al. |
| 6,965,702 B2 | 11/2005 | Gallagher |
| 6,966,906 B2 | 11/2005 | Brown |
| 6,974,411 B2 | 12/2005 | Belson |
| 6,997,871 B2 | 2/2006 | Sonnenschein et al. |
| 7,004,900 B2 | 2/2006 | Wendlandt et al. |
| 7,029,435 B2 | 4/2006 | Nakao |
| 7,041,050 B1 | 5/2006 | Ronald |
| 7,095,548 B1 | 8/2006 | Cho et al. |
| 7,103,228 B2 | 9/2006 | Kraft et al. |
| 7,116,352 B2 | 10/2006 | Yaron |
| 7,173,656 B1 | 2/2007 | Dunton et al. |
| 7,228,004 B2 | 6/2007 | Gallagher et al. |
| 7,280,141 B1 | 10/2007 | Frank et al. |
| 7,317,458 B2 * | 1/2008 | Wada .............................. 345/590 |
| 7,322,934 B2 | 1/2008 | Miyake et al. |
| 7,341,555 B2 | 3/2008 | Ootawara et al. |
| 7,362,911 B1 | 4/2008 | Frank |
| 7,405,877 B1 | 7/2008 | Schechterman |
| 7,435,218 B2 | 10/2008 | Krattiger et al. |
| 7,436,562 B2 | 10/2008 | Nagasawa et al. |
| 7,507,200 B2 | 3/2009 | Okada |

| | | |
|---|---|---|
| 7,551,196 B2 | 6/2009 | Ono et al. |
| 7,556,599 B2 | 7/2009 | Rovegno |
| 7,561,190 B2 | 7/2009 | Deng et al. |
| 7,621,869 B2 | 11/2009 | Ratnakar |
| 7,646,520 B2 | 1/2010 | Funaki et al. |
| 7,678,043 B2 | 3/2010 | Gilad |
| 7,683,926 B2 | 3/2010 | Schechterman et al. |
| 7,749,156 B2 | 7/2010 | Ouchi |
| 7,825,964 B2 | 11/2010 | Hoshino et al. |
| 7,864,215 B2 * | 1/2011 | Carlsson et al. ......... 348/211.11 |
| 7,910,295 B2 * | 3/2011 | Hoon et al. ................. 435/6.14 |
| 7,927,272 B2 | 4/2011 | Bayer et al. |
| 8,009,167 B2 | 8/2011 | Dekel et al. |
| 8,064,666 B2 | 11/2011 | Bayer |
| 8,070,743 B2 | 12/2011 | Kagan et al. |
| 2001/0007468 A1 * | 7/2001 | Sugimoto et al. ............... 348/71 |
| 2001/0037052 A1 | 11/2001 | Higuchi et al. |
| 2001/0051766 A1 | 12/2001 | Gazdzinski |
| 2001/0056238 A1 | 12/2001 | Tsujita |
| 2002/0026188 A1 | 2/2002 | Balbierz et al. |
| 2002/0039400 A1 | 4/2002 | Kaufman et al. |
| 2002/0089584 A1 | 7/2002 | Abe |
| 2002/0095168 A1 | 7/2002 | Griego et al. |
| 2002/0099267 A1 | 7/2002 | Wendlandt et al. |
| 2002/0101546 A1 | 8/2002 | Sharp et al. |
| 2002/0110282 A1 | 8/2002 | Kraft et al. |
| 2002/0115908 A1 | 8/2002 | Farkas et al. |
| 2002/0156347 A1 | 10/2002 | Kim et al. |
| 2002/0193662 A1 | 12/2002 | Belson |
| 2003/0004399 A1 | 1/2003 | Belson |
| 2003/0011768 A1 | 1/2003 | Jung et al. |
| 2003/0032863 A1 | 2/2003 | Kazakevich |
| 2003/0040668 A1 | 2/2003 | Kaneko et al. |
| 2003/0045778 A1 | 3/2003 | Ohline et al. |
| 2003/0065250 A1 | 4/2003 | Chiel et al. |
| 2003/0088152 A1 | 5/2003 | Takada |
| 2003/0093031 A1 | 5/2003 | Long et al. |
| 2003/0093088 A1 | 5/2003 | Long et al. |
| 2003/0103199 A1 | 6/2003 | Jung et al. |
| 2003/0105386 A1 | 6/2003 | Voloshin et al. |
| 2003/0120130 A1 | 6/2003 | Glukhovsky |
| 2003/0125630 A1 | 7/2003 | Furnish |
| 2003/0125788 A1 | 7/2003 | Long |
| 2003/0130711 A1 | 7/2003 | Pearson et al. |
| 2003/0153866 A1 | 8/2003 | Long et al. |
| 2003/0161545 A1 | 8/2003 | Gallagher |
| 2003/0167007 A1 | 9/2003 | Belson |
| 2003/0171650 A1 | 9/2003 | Tartaglia et al. |
| 2003/0176767 A1 | 9/2003 | Long et al. |
| 2003/0179302 A1 | 9/2003 | Harada et al. |
| 2003/0187326 A1 | 10/2003 | Chang |
| 2003/0195545 A1 | 10/2003 | Hermann et al. |
| 2003/0197781 A1 * | 10/2003 | Sugimoto et al. ............... 348/72 |
| 2003/0197793 A1 | 10/2003 | Mitsunaga et al. |
| 2003/0225433 A1 | 12/2003 | Nakao |
| 2003/0233115 A1 | 12/2003 | Eversull et al. |
| 2004/0023397 A1 | 2/2004 | Vig et al. |
| 2004/0034278 A1 | 2/2004 | Adams |
| 2004/0049096 A1 | 3/2004 | Adams |
| 2004/0059191 A1 | 3/2004 | Krupa et al. |
| 2004/0080613 A1 | 4/2004 | Moriyama |
| 2004/0097790 A1 | 5/2004 | Farkas et al. |
| 2004/0109164 A1 | 6/2004 | Horii et al. |
| 2004/0111019 A1 | 6/2004 | Long |
| 2004/0122291 A1 | 6/2004 | Takahashi |
| 2004/0141054 A1 | 7/2004 | Mochida et al. |
| 2004/0158124 A1 | 8/2004 | Okada |
| 2004/0207618 A1 | 10/2004 | Williams et al. |
| 2004/0242987 A1 | 12/2004 | Liew et al. |
| 2005/0010084 A1 | 1/2005 | Tsai |
| 2005/0014996 A1 | 1/2005 | Konomura et al. |
| 2005/0020918 A1 | 1/2005 | Wilk et al. |
| 2005/0020926 A1 | 1/2005 | Wiklof et al. |
| 2005/0038317 A1 | 2/2005 | Ratnakar |
| 2005/0038319 A1 | 2/2005 | Goldwasser et al. |
| 2005/0068431 A1 | 3/2005 | Mori |
| 2005/0085693 A1 | 4/2005 | Belson et al. |
| 2005/0085790 A1 | 4/2005 | Guest et al. |
| 2005/0096502 A1 | 5/2005 | Khalili |
| 2005/0154278 A1 | 7/2005 | Cabiri et al. |
| 2005/0165272 A1 | 7/2005 | Okada et al. |
| 2005/0165279 A1 | 7/2005 | Adler et al. |
| 2005/0177024 A1 | 8/2005 | Mackin |
| 2005/0203420 A1 | 9/2005 | Kleen et al. |
| 2005/0215911 A1 | 9/2005 | Alfano et al. |
| 2005/0222500 A1 * | 10/2005 | Itoi .............................. 600/180 |
| 2005/0228224 A1 | 10/2005 | Okada et al. |
| 2005/0267361 A1 | 12/2005 | Younker et al. |
| 2005/0272975 A1 | 12/2005 | McWeeney et al. |
| 2005/0272977 A1 | 12/2005 | Saadat et al. |
| 2006/0044267 A1 | 3/2006 | Xie et al. |
| 2006/0052709 A1 | 3/2006 | DeBaryshe et al. |
| 2006/0058584 A1 | 3/2006 | Hirata |
| 2006/0106286 A1 | 5/2006 | Wendlandt et al. |
| 2006/0149127 A1 | 7/2006 | Seddiqui et al. |
| 2006/0149129 A1 | 7/2006 | Watts et al. |
| 2006/0183975 A1 | 8/2006 | Saadat et al. |
| 2006/0217594 A1 | 9/2006 | Ferguson |
| 2006/0279632 A1 | 12/2006 | Anderson |
| 2006/0285766 A1 | 12/2006 | Ali |
| 2006/0293562 A1 | 12/2006 | Uchimura et al. |
| 2007/0015967 A1 | 1/2007 | Boulais et al. |
| 2007/0015989 A1 | 1/2007 | Desai et al. |
| 2007/0083081 A1 | 4/2007 | Schlagenhauf et al. |
| 2007/0103460 A1 | 5/2007 | Zhang et al. |
| 2007/0142711 A1 | 6/2007 | Bayer et al. |
| 2007/0173686 A1 | 7/2007 | Lin et al. |
| 2007/0177008 A1 | 8/2007 | Bayer et al. |
| 2007/0177009 A1 | 8/2007 | Bayer et al. |
| 2007/0183685 A1 | 8/2007 | Wada et al. |
| 2007/0185384 A1 | 8/2007 | Bayer et al. |
| 2007/0225552 A1 | 9/2007 | Segawa et al. |
| 2007/0225734 A1 | 9/2007 | Bell et al. |
| 2007/0238927 A1 | 10/2007 | Ueno et al. |
| 2007/0244354 A1 | 10/2007 | Bayer |
| 2007/0279486 A1 | 12/2007 | Bayer et al. |
| 2007/0280669 A1 | 12/2007 | Karim |
| 2007/0293720 A1 | 12/2007 | Bayer |
| 2008/0021269 A1 | 1/2008 | Tinkham et al. |
| 2008/0021274 A1 | 1/2008 | Bayer et al. |
| 2008/0033450 A1 | 2/2008 | Bayer et al. |
| 2008/0039693 A1 | 2/2008 | Karasawa |
| 2008/0064931 A1 | 3/2008 | Schena et al. |
| 2008/0065110 A1 | 3/2008 | Duval et al. |
| 2008/0071291 A1 | 3/2008 | Duval et al. |
| 2008/0079827 A1 | 4/2008 | Hoshino et al. |
| 2008/0097292 A1 | 4/2008 | Cabiri et al. |
| 2008/0114288 A1 | 5/2008 | Whayne et al. |
| 2008/0130108 A1 | 6/2008 | Bayer et al. |
| 2008/0154288 A1 | 6/2008 | Belson |
| 2008/0199829 A1 | 8/2008 | Paley et al. |
| 2008/0275298 A1 | 11/2008 | Ratnakar |
| 2009/0015842 A1 | 1/2009 | Leitgeb et al. |
| 2009/0023998 A1 | 1/2009 | Ratnakar |
| 2009/0036739 A1 | 2/2009 | Hadani |
| 2009/0049627 A1 | 2/2009 | Kritzler |
| 2009/0082629 A1 | 3/2009 | Dotan et al. |
| 2009/0105538 A1 | 4/2009 | Van Dam et al. |
| 2009/0137867 A1 | 5/2009 | Goto |
| 2009/0213211 A1 | 8/2009 | Bayer et al. |
| 2009/0231419 A1 | 9/2009 | Bayer et al. |
| 2010/0217076 A1 | 8/2010 | Ratnakar |
| 2011/0160535 A1 | 6/2011 | Bayer et al. |
| 2011/0213206 A1 | 9/2011 | Boutillette et al. |

FOREIGN PATENT DOCUMENTS

| | | |
|---|---|---|
| CN | 1628603 A | 6/2005 |
| DE | 196 26433 | 1/1998 |
| DE | 19626433 A1 | 1/1998 |
| DE | 20 2006 017 173 U1 | 3/2007 |
| EP | 0 586 162 | 3/1994 |
| EP | 1 570 778 | 9/2005 |
| EP | 1 769 720 A1 | 4/2007 |
| FR | 711 949 | 9/1931 |
| JP | 49-130235 A | 12/1974 |
| JP | 56-9712 A | 1/1981 |
| JP | 62-094312 U | 6/1987 |
| JP | 63-309912 A | 12/1988 |

| | | | |
|---|---|---|---|
| JP | 3-159629 A | 7/1991 | |
| JP | 5-341210 A | 12/1993 | |
| JP | 6-130308 A | 5/1994 | |
| JP | 7-352 A | 1/1995 | |
| JP | 7-354 A | 1/1995 | |
| JP | 7-021001 U | 4/1995 | |
| JP | 8-206061 A | 8/1996 | |
| JP | 7-136108 A | 5/1998 | |
| JP | 11-76150 A | 3/1999 | |
| WO | WO 93/15648 | 8/1993 | |
| WO | WO-99/17542 A1 | 4/1999 | |
| WO | WO-99/30506 A1 | 6/1999 | |
| WO | WO 02/085194 | 10/2002 | |
| WO | WO-02085194 A1 | 10/2002 | |
| WO | WO-02/084105 A3 | 11/2002 | |
| WO | WO-02/094105 A2 | 11/2002 | |
| WO | WO-2006/073676 A1 | 7/2006 | |
| WO | WO-2006073725 A1 | 7/2006 | |
| WO | WO-2006/110275 A2 | 10/2006 | |
| WO | WO-2006/110275 A3 | 10/2006 | |
| WO | WO-2007/015241 A2 | 2/2007 | |
| WO | WO-2007/015241 A3 | 2/2007 | |
| WO | WO-2007070644 A2 | 6/2007 | |
| WO | WO-2007087421 A2 | 8/2007 | |
| WO | WO-2007092533 A2 | 8/2007 | |
| WO | WO-2007092636 A2 | 8/2007 | |
| WO | WO-2007136859 A2 | 11/2007 | |
| WO | WO-2007136879 A2 | 11/2007 | |
| WO | WO-2009/015396 A2 | 1/2009 | |
| WO | WO-2009/015396 A3 | 1/2009 | |
| WO | WO-2009014895 A1 | 1/2009 | |
| WO | WO-2009/049322 A2 | 4/2009 | |
| WO | WO-2009/049322 A3 | 4/2009 | |
| WO | WO-2009062179 A1 | 5/2009 | |

OTHER PUBLICATIONS

U.S. Appl. No. 11/834,540, filed Aug. 6, 2007, Bayer.
Invitation to Pay Additional Fees for PCT/US2007/002096, filed Jan. 23, 2007, mailed Jul. 6, 2007, 4 pgs.
Invitation to Pay Additional Fees for PCT/US2007/003631, filed Feb. 9, 2007, mailed Aug. 7, 2007, 5 pgs.
Invitation to Pay Additional Fees for PCT/US2007/003322, filed Feb. 6, 2007, mailed Aug. 7, 2007, 6 pgs.
U.S. Appl. No. 11/153,007, filed Jun. 14, 2005, Seddiqui et al.
U.S. Appl. No. 11/160,646, filed Jul. 1, 2005, Desai et al.
U.S. Appl. No. 11/215,660, filed Aug. 29, 2005, Watts et al.
U.S. Appl. No. 11/609,838, filed Dec. 12, 2006, Bayer et al.
U.S. Appl. No. 11/626,189, filed Jan. 23, 2007, Bayer et al.
U.S. Appl. No. 11/673,470, filed Feb. 9, 2007, Bayer et al.
U.S. Appl. No. 11/672,020, filed Feb. 6, 2007, Bayer et al.
U.S. Appl. No. 11/736,438, filed Apr. 17, 2007, Bayer.
U.S. Appl. No. 11/751,597, filed May. 21, 2007, Bayer et al.
U.S. Appl. No. 11/751,605, filed May. 21, 2007, Diel et al.
International Search Report for PCT/US2005/044624, filed Dec. 8, 2005, mailed May 19, 2006, 16 pgs.
International Search Report for PCT/US2006/047748, filed Dec. 13, 2006, mailed Jun. 20, 2007, 12 pgs.
International Search Report for PCT/US2008/069435, filed Jul. 8, 2008, mailed Oct. 23, 2008, 8 pgs.
Invitation to Pay Additional Fees for PCT/US2008/071390, filed Jul. 28, 2008, mailed Nov. 11, 2008, 5 pgs.
International Search Report for PCT/US2007/012358 filed May 21, 2007, mailed Dec. 11, 2007, 6 pgs.
"European Application Serial No. 07795177.0, Office Action mailed Jun. 14, 2011", 6 pgs.
"European Application Serial No. 07777255.6, Communication dated Jan. 22, 2009", 2 pgs.
"European Application Seriai No. 07777255.6, Response fiied Feb. 6, 2009 to Communication dated Jan. 22, 2009", 6 pgs.
"U.S. Appl. No. 11/215,660, Final Office Action mailed Oct. 8, 2009", 12 pgs.
"U.S. Appl. No. 11/215,660, Non Final Office Action mailed Mar. 25, 2009", 11 pgs.
"U.S. Appl. No. 11/215,660, Non-Final Office Action mailed Mar. 29, 2010", 16 pgs.
"U.S. Appl. No. 11/215,660, Response filed Jan. 26, 2009 to Restriction Requirement mailed Oct. 30, 2008", 2 pgs.
"U.S. Appl. No. 11/215,660, Response filed Mar. 8, 2010 to Final Office Action mailed Oct. 8, 2009", 11 pgs.
"U.S. Appl. No. 11/215,660, Response filed Jun. 29, 2009 to Non Final Office Action mailed Mar. 25, 2009", 9 pgs.
"U.S. Appl. No. 11/215,660, Restriction Requirement mailed Oct. 30, 2008", 7 pgs.
"U.S. Appl. No. 11/609,838, Non-Final Office Action mailed Apr. 6, 2010", 28 pgs.
"U.S. Appl. No. 11/609,838, Response filed Jun. 28, 2010 to Non Final Office Action mailed Apr. 6, 2010", 14 pgs.
"U.S. Appl. No. 11/626,189, Restriction Requirement mailed Aug. 10, 2010", 5 pgs.
"U.S. Appl. No. 11/751,605, Response filed Jul. 23, 2010 to Restriction Requirement mailed Jun. 25, 2010", 9 pgs.
"U.S. Appl. No. 11/751,605, Restriction Requirement mailed Jun. 25, 2010", 9 pgs.
"U.S. Appl. No. 11/828,835, Non-Final Office Action mailed Oct. 28, 2010", 11 pgs.
"U.S. Appl. No. 11/828,835, Final Office Action mailed Mar. 22, 2011", 12 pgs.
"U.S. Appl. No. 11/828,835, Response filed Feb. 9, 2011 to Non Final Office Action mailed Oct. 28, 2010", 10 pgs.
"U.S. Appl. No. 11/828,835, Response filed May 24, 2011 to Final Office Action mailed Mar. 22, 2011", 13 pgs.
"U.S. Appl. No. 11/828,835, Response filed Oct. 21, 2010 to Restriction Requirement mailed Sep. 21, 2010", 7 pgs.
"U.S. Appl. No. 11/828,835, Restriction Requirement mailed Sep. 21, 2010", 6 pgs.
"European Application Serial No. 06845440.4, Office Action mailed Feb. 5, 2010", 4 pgs.
"European Application Serial No. 06845440.4, Office Action Response filed Jul. 8, 2010", 16 pgs.
"European Application Serial No. 07717235.1, Office Action mailed Apr. 1, 2010", 2 pgs.
"European Application Serial No. 07763368.3, Office Action mailed May 5, 2009", 3 pgs.
"European Application Serial No. 07763368.3, Response filed Nov. 11, 2009 to Office Action mailed May 5, 2009", 10 pgs.
"International Application No. PCT/US2005/045499, Search Report mailed May 18, 2006", 4 pgs.
"International Application No. PCT/US2006/047748, Search Report mailed Jun. 20, 2007", 3 pgs.
"International Application No. PCT/US2007/003631, Internaional Search Report mailed Oct. 26, 2007", 5 pgs.
"International Application No. PCT/US2007/003631, Written Opinion mailed Oct. 26, 2007", 7 pgs.
"International Application No. PCT/US2008/083034, Search Report mailed Mar. 13, 2009", 3 pgs.
"International Application No. PCT/US2008/083034, Written Opinion mailed Mar. 13, 2009", 4 pgs.
Amendment in Response to Non-Final Office Action filed on Dec. 16, 2011, for U.S. Appl. No. 11/938,256, filed Nov. 10, 2007, 10 pages.
Amendment in Response to Non-Final Office Action filed on Feb. 15, 2012, for U.S. Appl. No. 11/626,189, filed Jan. 23, 2007, 13 pages.
Amendment in Response to Non-Final Office Action filed on Feb. 17, 2012, for U.S. Appl. No. 11/751,597, filed May 21, 2007, 18 pages.
Non-Final Office Action mailed on Feb. 13, 2012, for U.S. Appl. No. 13/275,206, filed Oct. 17, 2011, 13 pages.
Non-Final Office Action mailed on Feb. 14, 2012, for U.S Appl. No. 12/251,383, filed Oct. 14, 2008, 9 pages.
Notice of Allowance mailed on Feb. 8, 2012, for U.S. Appl. No. 11/609,838, filed Dec. 12, 2006, 8 pages.
Response to European Office Action filed on Dec. 13, 2011, for European Patent Application No. 07795177.0, filed on May 21, 2007, 9 pages.
Advisory Action mailed on Nov. 2, 2010, for U.S. Appl. No. 11/609,838, filed Dec. 12, 2006, 3 pages.
Advisory Action mailed on May 23, 2011, for U.S. Appl. No. 11/751,605, filed May 21, 2007, 3 pages.

Amendment in Response to Non-Final Office Action filed on Aug. 30, 2010, for U.S. Appl. No. 11/215,660, filed Aug. 29, 2005, 17 pages.
Amendment in Response to Final Office Action filed on Oct. 22, 2010, for U.S. Appl. No. 11/609,838, filed Dec. 12, 2006, 15 pages.
Amendment in Response to Non-Final Office Action filed on Oct. 22, 2010, for U.S. Appl. No. 11/834,540, filed Aug. 6, 2007, 13 pages.
Amendment in Response to Non-Final Office Action filed on Feb. 25, 2011, for U.S. Appl. No. 11/751,605, filed May 21, 2007, 15 pages.
Amendment in Response to Final Office Action filed on Feb. 28, 2011, for U.S. Appl. No. 11/215,660, filed Aug. 29, 2005, 11 pages.
Amendment in Response to Non-Final Office Action filed on Apr. 12, 2011, for U.S. Appl. No. 11/626,189, filed Jan. 23, 2007, 18 pages.
Amendment in Response to Non-Final Office Action filed on May 17, 2011, for U.S. Appl. No. 11/609,838, filed Dec. 12, 2006, 18 pages.
Amendment in Response to Final Office Action filed on May 17, 2011, for U.S. Appl. No. 11/751,605, filed May 21, 2007, 10 pages.
Amendment in Response to Non-Final Office Action filed on May 24, 2011, for U.S. Appl. No. 11/736,438, filed Apr. 17, 2007, 11 pages.
Amendment in Response to Non-Final Office Action filed on Jun. 6, 2011, for U.S. Appl. No. 12/101,050, filed Apr. 10, 2008, 17 pages.
Amendment in response to Final Office Action filed on Jun. 7, 2011, for U.S. Appl. No. 11/751,605, filed May 21, 2007, 11 pages.
Amendment in Response to Final Office Action filed on Dec. 7, 2011, for U.S. Appl. No. 11/736,438, filed Apr. 17, 2007, 10 pages.
European Office Action mailed on Nov. 8, 2010, for European Patent Application No. 05854262.2, filed on Dec. 8, 2005, 5 pages.
Final Office Action mailed on Aug. 23, 2010, for U.S. Appl. No. 11/609,838, filed Dec. 12, 2006, 20 pages.
Final Office Action mailed on Nov. 1, 2010, for U.S. Appl. No. 11/215,660, filed Aug. 29, 2005, 12 pages.
Final Office Action mailed on Apr. 29, 2011, for U.S. Appl. No. 11/751,605, filed on May 21, 2007, 9 pages.
Final Office Action mailed on Aug. 3, 2011, for U.S. Appl. No. 11/736,438, filed on Apr. 17, 2007, 11 pages.
International Search Report mailed on Sep. 28, 2007, for PCT Patent Application No. PCT/US2007/002096 filed on Jan. 23, 2007, 4 pages.
International Search Report mailed on Oct. 25, 2007, for PCT Patent Application No. PCT/US2007/003322, filed on Feb. 6, 2007, 5 pages.
International Search Report mailed on Jan. 28, 2008, for PCT Patent Application No. PCT/US2007/012189, filed on May 21, 2007, 2 pages.
International Search Report mailed on Feb. 25, 2009, for PCT Patent Application No. PCT/US2008/071390, filed on Jul. 28, 2008, 2 pages.
International Search Report mailed on Mar. 13, 2009, for PCT Patent Application No. PCT/US2008/079891, filed on Nov. 10, 2008, 2 pages.
International Search Report mailed on Apr. 6, 2009, for PCT Patent Application No. PCT/US2008/079878, filed on Oct. 14, 2008, 3 pages.
Invitation to Pay Additional Fees mailed on Dec. 29, 2008, for PCT Patent Application No. PCT/US2008/079891, filed on Oct. 14, 2008, 7 pages.
Japanese Office Action mailed on Jul. 19, 2011, for Japanese Patent Application No. 2007-550378, filed on Dec. 8, 2005, with English Translation, 11 pages.
Non-Final Office Action mailed on Jan. 10, 2008, for U.S. Appl. No. 11/160,646, filed Jul. 1, 2005, 6 pages.
Non-Final Office Action mailed on Mar. 12, 2008, for U.S. Appl. No. 11/153,007, filed Jun. 14, 2005, 11 pages.
Non-Final Office Action mailed on Aug. 24, 2010, for U.S. Appl. No. 11/834,540, filed Aug. 6, 2007, 11 pages.
Non-Final Office Action mailed on Oct. 18, 2010, for U.S. Appl. No. 11/626,189, filed Jan. 23, 2007, 11 pages.
Non-Final Office Action mailed on Dec. 22, 2010, for U.S. Appl. No. 11/751,605, filed May 21, 2007, 10 pages.
Non-Final Office Action mailed on Feb. 17, 2011, for U.S. Appl. No. 11/609,838, filed Dec. 12, 2006, 24 pages.
Non-Final Office Action mailed on Mar. 2, 2011, for U.S. Appl. No. 11/736,438, filed Apr. 17, 2007, 10 pages.
Non-Final Office Action mailed on May 23, 2011, for U.S. Appl. No. 12/101,050, filed Apr. 10, 2008, 11 pages.
Non-Final Office Action mailed on Jun. 28, 2011, for U.S. Appl. No. 11/938,256, filed Nov. 10, 2007, 23 pages.
Non-Final Office Action mailed on Aug. 4, 2011, for U.S. Appl. No. 11/609,838, filed Dec. 12, 2006, 16 pages.
Non-Final Office Action mailed on Aug. 15, 2011, for U.S. Appl. No. 11/626,189, filed Jan. 23, 2007, 13 pages.
Non-Final Office Action mailed on Aug. 18, 2011, for U.S. Appl. No. 11/751,597, filed May 21, 2007, 25 pages.
Non-Final Office Action mailed on Oct. 21, 2011, for PCT U.S. Appl. No. 12/251,406, filed Oct. 14, 2008, 8 pages.
Non-Final Office Action mailed on Oct. 26, 2011, for U.S. Appl. No. 11/673,470, filed Feb. 9, 2007, 40 pages.
Non-Final Office Action mailed on Nov. 23, 2011, for U.S. Appl. No. 11/672,020, filed Feb. 6, 2007, 12 pages.
Notice of Allowance mailed on Dec. 13, 2010, for U.S. Appl. No. 11/834,540, filed Aug. 6, 2007, 4 pages.
Notice of Allowance mailed on Jul. 22, 2011, for U.S. Appl. No. 12/101,050, filed Apr. 10, 2008, 7 pages.
Preliminary Amendment filed Jan. 26, 2009, for U.S. Appl. No. 11/672,020, filed Feb. 6, 2007, filed Feb. 6, 2007, 11 pages.
Response to European Office Action filed on Aug. 18, 2010, for European Patent Application No. 07717235.1, filed Feb. 9, 2007, 7 pages.
Response to European Office Action filed on Mar. 8, 2011, for European Patent Application No. 05854262.2, filed on Dec. 8, 2005, 11 pages.
Response to Restriction Requirement filed on Aug. 4, 2010, for U.S. Appl. No. 11/834,540, filed Aug. 6, 2007, 5 pages.
Response to Restriction Requirement filed on Sep. 9, 2010, for U.S. Appl. No. 11/626,189, filed Jan. 23, 2007, 8 pages.
Response to Restriction Requirement filed on Feb. 8, 2011, for U.S. Appl. No. 11/736,438, filed Apr. 17, 2007, 8 pages.
Response to Restriction Requirement filed on Apr. 27, 2011, for U.S. Appl. No. 12/101,050, filed Apr. 10, 2008, 11 pages.
Restriction Requirement mailed on Jul. 13, 2010, for U.S. Appl. No. 11/834,540, filed Aug. 6, 2007, 8 pages.
Restriction Requirement mailed on Dec. 10, 2010, for U.S. Appl. No. 11/736,438, filed Apr. 17, 2007, 16 pages.
Restriction Requirement mailed on Mar. 11, 2011, for U.S. Appl. No. 12/101,050, filed Apr. 10, 2008, 6 pages.
Restriction Requirement mailed on Sep. 29, 2011, for U.S. Appl. No. 11/672,020, filed Feb. 6, 2007, 6 pages.
Restriction Requirement mailed on Nov. 28, 2011, for U.S. Appl. No. 12/251,383, filed Oct. 14, 2008, 6 pages.
Substitute Preliminary Amendment filed Mar. 8, 2010, for U.S. Appl. No. 11/672,020, filed Feb. 6, 2007, 2 pages.
Written Opinion of the International Searching Authority mailed on May 18, 2006, for PCT Patent Application No. PCT/US2005/045499, filed on Dec. 8, 2005, 9 pages.
Written Opinion of the International Searching Authority mailed on May 19, 2006, for PCT Patent Application No. PCT/US2005/044624, filed on Dec. 8, 2005, 8 pages.
Written Opinion of the International Searching Authority mailed on Jun. 20, 2007, for PCT Patent Application No. PCT/US2006/047748, filed on Dec. 13, 2006, 7 pages.
Written Opinion of the International Searching Authority mailed on Sep. 28, 2007, for PCT Patent Application No. PCT/US2007/002096 filed on Jan. 23, 2007, 8 pages.
Written Opinion of the International Searching Authority mailed on Oct. 25, 2007, for PCT Patent Application No. PCT/US2007/003322, filed on Feb. 6, 2007, 9 pages
Written Opinion of the International Searching Authority mailed on Dec. 11, 2007, for PCT Patent Application No. PCT/US2007/012358, filed on May 21, 2007, 6 pages.

Written Opinion of the International Searching Authority mailed on Jan. 28, 2008, for PCT Patent Application No. PCT/US2007/012189, filed on May 21, 2007, 7 pages.

Written Opinion of the International Searching Authority mailed on Oct. 23, 2008, for PCT Patent Application No. PCT/US2008/069435, filed on Jul. 8, 2008, 6 pages.

Written Opinion of the International Searching Authority mailed on Feb. 25, 2009, for PCT Patent Application No. PCT/US2008/071390, filed on Jul. 28, 2008, 7 pages.

Written Opinion of International Searching Authority mailed on Mar. 13, 2009, for PCT Patent Application No. PCT/US2008/079891, filed on Nov. 10, 2008, 5 pages.

Written Opinion of International Searching Authority mailed on Apr. 6, 2009, for PCT Patent Application No. PCT/US2008/079878, filed on Oct. 14, 2008, 13 pages.

Response to Restriction Requirement filed on Oct. 31, 2011, for U.S. Appl. No. 11/672,020, filed Feb. 6, 2007, 3 pages.

* cited by examiner

SYSTEM AND METHOD FOR PRODUCING AND IMPROVING IMAGES

This application claims the benefit of U.S. Provisional Patent Application No. 60/801,748, filed May 19, 2006, the entire disclosure of which is incorporated herein by reference.

TECHNICAL FIELD OF THE INVENTION

The present invention relates to a system and method for producing and improving images.

BACKGROUND OF THE INVENTION

Multiple endoscopic devices with multiple cameras and light sources may be used for medical procedures, inspection of small pipes, or remote monitoring. For example, such an endoscopic device may be a medical endoscope comprising a flexible tube, and a camera and a light source mounted on the distal end of the flexible tube. The endoscope is insertable into an internal body cavity through a body orifice to examine the body cavity and tissues for diagnosis. The tube of the endoscope has one or more longitudinal channels, through which an instrument can reach the body cavity to take samples of suspicious tissues or to perform other surgical procedures such as polypectomy.

There are many types of endoscopes, and they are named in relation to the organs or areas with which they are used. For example, gastroscopes are used for examination and treatment of the esophagus, stomach and duodenum; colonoscopes for the colon; bronchoscopes for the bronchi; laparoscopes for the peritoneal cavity; sigmoidoscopes for the rectum and the sigmoid colon; arthroscopes for joints; cystoscopes for the urinary bladder; and angioscopes for the examination of blood vessels.

Each endoscope has a single forward viewing camera mounted at the distal end of the flexible tube to transmit an image to an eyepiece or video camera at the proximal end. The camera is used to assist a medical professional in advancing the endoscope into a body cavity and looking for abnormalities. The camera provides the medical professional with a two-dimensional view from the distal end of the endoscope. To capture an image from a different angle or in a different portion, the endoscope must be repositioned or moved back and forth. Repositioning and movement of the endoscope prolongs the procedure and causes added discomfort, complications, and risks to the patient. Additionally, in an environment similar to the lower gastro-intestinal tract, flexures, tissue folds and unusual geometries of the organ may prevent the endoscope's camera from viewing all areas of the organ. The unseen area may cause a potentially malignant (cancerous) polyp to be missed.

This problem can be overcome by providing an auxiliary camera and an auxiliary light source. The auxiliary camera and light source can be oriented to face the main camera and light source, thus providing an image of areas not viewable by the endoscope's main camera. This arrangement of cameras and light sources can provide both front and rear views of an area or an abnormality. In the case of polypectomy where a polyp is excised by placing a wire loop around the base of the polyp, the camera arrangement allows better placement of the wire loop to minimize damage to the adjacent healthy tissue.

SUMMARY OF THE INVENTION

The present invention relates to devices and methods for producing and improving video images generated by the imaging devices of endoscopes.

In accordance with one aspect of the invention, a method for displaying images includes adjusting at least one characteristic of an image from a first imaging device of an endoscope to match at least one corresponding characteristic of an image from a second imaging device of the endoscope. The characteristic may be one or more of color, contrast and brightness.

In a preferred embodiment, the adjusting step includes creating a histogram for each of RGB colors for the image from the first imaging device and a histogram for each of the RGB colors for the image from the second imaging device; adjusting the gamut of each histogram of the image from the first imaging device to match the gamut of the corresponding histogram of the image from the second imaging device; and using gamma coefficients to adjust a color level of each histogram of the image from the first imaging device to match a color level of the corresponding histogram of the image from the second imaging device.

In accordance with another aspect of the invention, a method for displaying images includes placing, side by side, an image from a first imaging device of an endoscope and an image from a second imaging device of the endoscope, wherein the imaging devices face each other; and reversing one of the images left for right.

In accordance with still another aspect of the invention, a method for sizing images includes placing an image from a first imaging device of an endoscope and an image from a second imaging device of the endoscope on a display device; and sizing the images so that an object, when placed at the same distance from the imaging devices, appears to have about the same size in the images.

In accordance with yet another aspect of the invention, a method for processing images includes placing image data from first and second imaging devices of an endoscope in one computer file for simultaneous display on a display device. Preferably, the image data from the imaging devices are time-correlated.

In a preferred embodiment, patient information data is also placed in the computer file for simultaneous display with the images on the display device.

In a further preferred embodiment, a time stamp is placed in the computer file for simultaneous display with the images and patient information data on the display device.

In accordance with still yet another aspect of the invention, an endoscopic system includes an endoscope that has a first imaging device and a second imaging device, and a controller that adjusts at least one characteristic of an image from the first imaging device of the endoscope to match at least one corresponding characteristic of an image from the second imaging device of the endoscope. The at least one characteristic may be one or more of color, contrast and brightness.

In a preferred embodiment, the controller creates a histogram for each of RGB colors for the image from the first imaging device and a histogram for each of the RGB colors for the image from the second imaging device; adjusts the gamut of each histogram of the image from the first imaging device to match the gamut of the corresponding histogram of the image from the second imaging device; and uses gamma coefficients to adjust a color level of each histogram of the image from the first imaging device to match a color level of the corresponding histogram of the image from the second imaging device.

In accordance with a further aspect of the invention, an endoscopic system includes an endoscope including a first imaging device and a second imaging device, and a display device that displays, side by side, an image from the first imaging device of the endoscope and an image from the second imaging device of the endoscope, wherein the imaging devices face each other, and wherein one of the images is reversed left for right.

In accordance with a still further aspect of the invention, an endoscopic system includes an endoscope including a first imaging device and a second imaging device, and a display device that displays an image from the first imaging device of the endoscope and an image from the second imaging device of the endoscope, wherein the images are sized so that an object, when placed at the same distance from the imaging devices, appears to have about the same size in the images.

In accordance with a yet further aspect of the invention, an endoscopic system includes an endoscope including a first imaging device and a second imaging device, and a controller that places image data from the first and second imaging devices of the endoscope in one computer file for simultaneous display on a display device. Preferably, the image data from the imaging devices are time-correlated.

In a preferred embodiment, patient information data is also placed in the computer file for simultaneous display with the images on the display device.

In a further preferred embodiment, a time stamp is placed in the computer file for simultaneous display with the images and patient information data on the display device.

DETAILED DESCRIPTION OF EMBODIMENTS OF THE INVENTION

Figure 1:
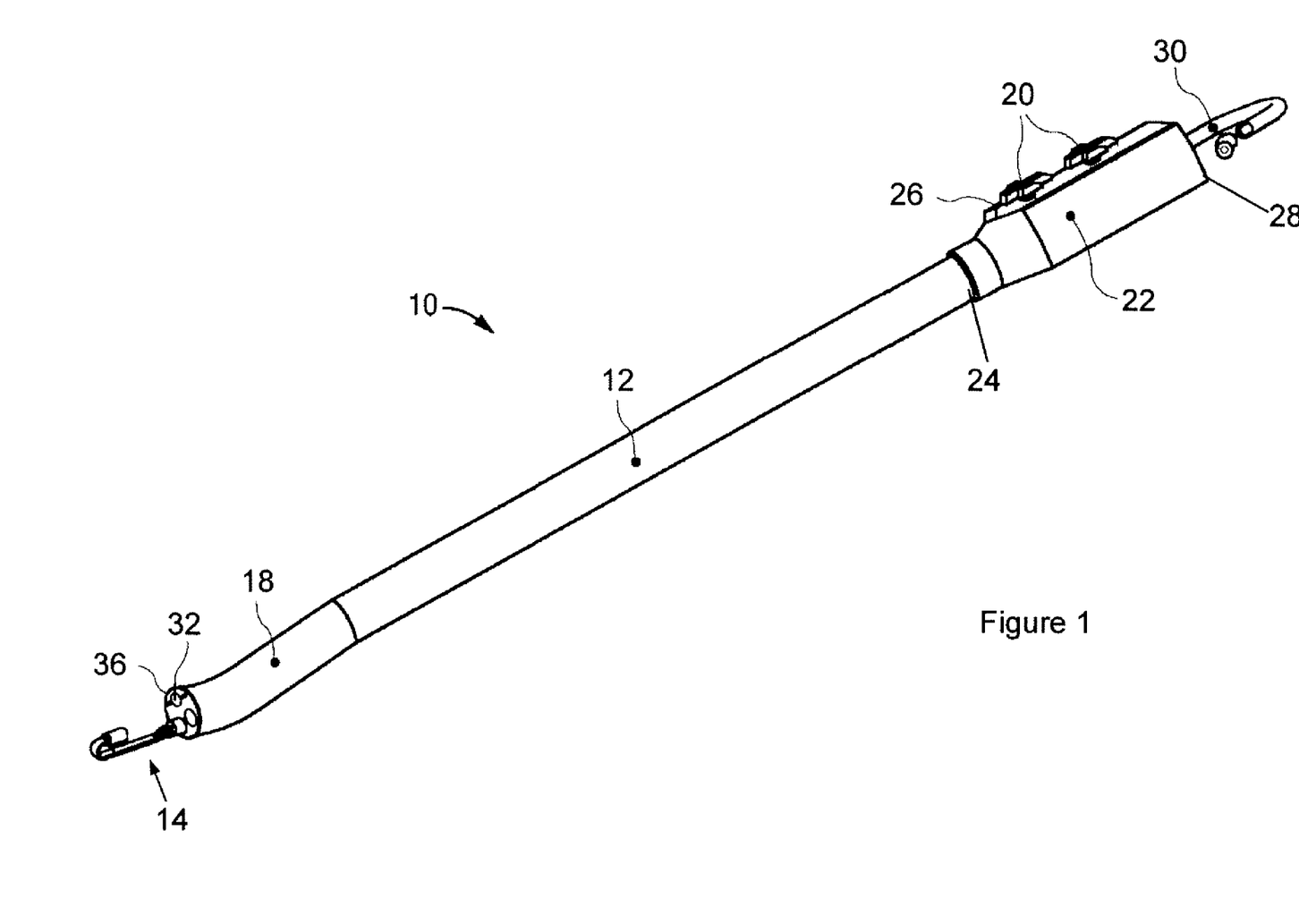
FIG. 1 shows a perspective view of an endoscope with an imaging assembly according to one embodiment of the present invention.

FIG. 1 illustrates an exemplary endoscope 10 of the present invention. This endoscope 10 can be used in a variety of medical procedures in which imaging of a body tissue, organ, cavity or lumen is required. The types of procedures include, for example, anoscopy, arthroscopy, bronchoscopy, colonoscopy, cystoscopy, EGD, laparoscopy, and sigmoidoscopy.

Figure 2:
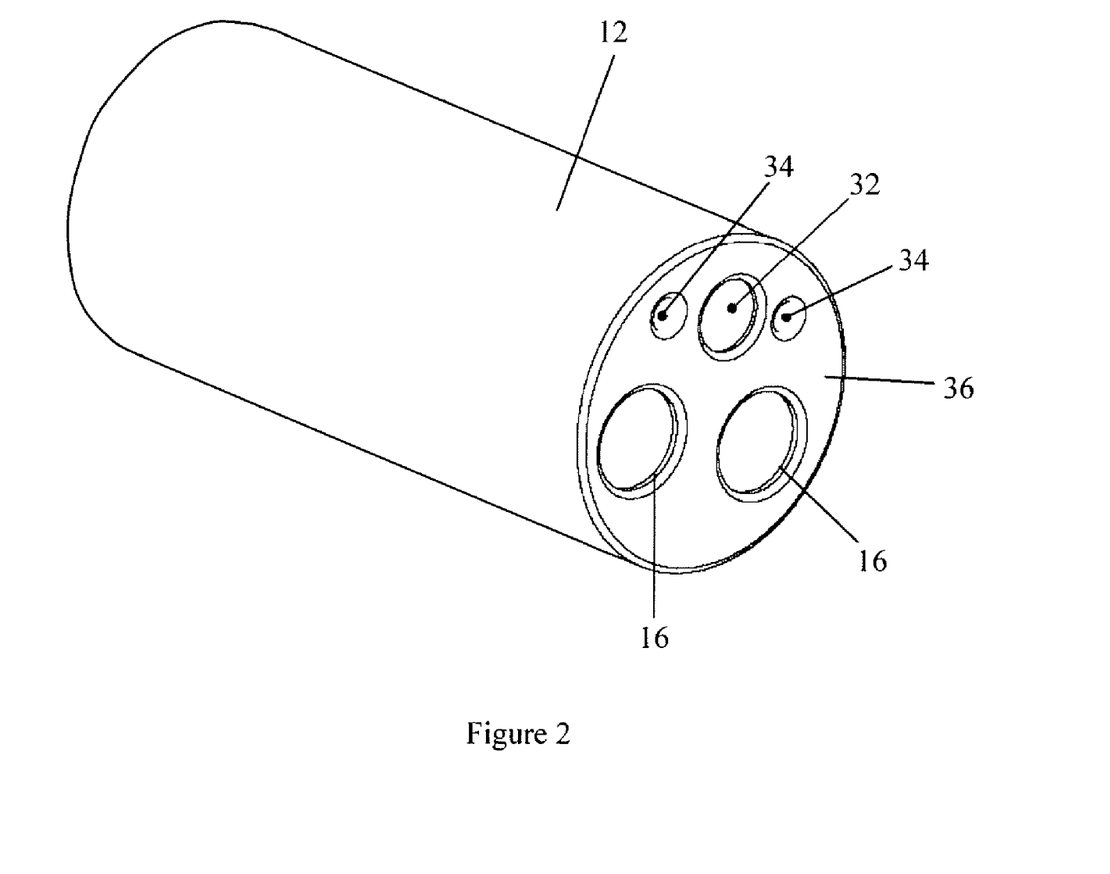
FIG. 2 shows a perspective view of the distal end of an insertion tube of the endoscope of FIG. 1.

The endoscope 10 of FIG. 1 includes an insertion tube 12 and an imaging assembly 14, a section of which is housed inside the insertion tube 12. As shown in FIG. 2, the insertion tube 12 has two longitudinal channels 16. In general, however, the insertion tube 12 may have any number of longitudinal channels. An instrument can reach the body cavity through one of the channels 16 to perform any desired procedures, such as to take samples of suspicious tissues or to perform other surgical procedures such as polypectomy. The instruments may be, for example, a retractable needle for drug injection, hydraulically actuated scissors, clamps, grasping tools, electrocoagulation systems, ultrasound transducers, electrical sensors, heating elements, laser mechanisms and other ablation means. In some embodiments, one of the channels can be used to supply a washing liquid such as water for washing. Another or the same channel may be used to supply a gas, such as $CO_2$ or air into the organ. The channels 16 may also be used to extract fluids or inject fluids, such as a drug in a liquid carrier, into the body. Various biopsy, drug delivery, and other diagnostic and therapeutic devices may also be inserted via the channels 16 to perform specific functions.

The insertion tube 12 preferably is steerable or has a steerable distal end region 18 as shown in FIG. 1. The length of the distal end region 18 may be any suitable fraction of the length of the insertion tube 12, such as one half, one third, one fourth, one sixth, one tenth, or one twentieth. The insertion tube 12 may have control cables (not shown) for the manipulation of the insertion tube 12. Preferably, the control cables are symmetrically positioned within the insertion tube 12 and extend along the length of the insertion tube 12. The control cables may be anchored at or near the distal end 36 of the insertion tube 12. Each of the control cables may be a Bowden cable, which includes a wire contained in a flexible overlying hollow tube. The wires of the Bowden cables are attached to controls 20 in the handle 22. Using the controls 20, the wires can be pulled to bend the distal end region 18 of the insertion tube 12 in a given direction. The Bowden cables can be used to articulate the distal end region 18 of the insertion tube 12 in different directions.

As shown in FIG. 1, the endoscope 10 may also include a control handle 22 connected to the proximal end 24 of the insertion tube 12. Preferably, the control handle 22 has one or more ports and/or valves (not shown) for controlling access to the channels 16 of the insertion tube 12. The ports and/or valves can be air or water valves, suction valves, instrumentation ports, and suction/instrumentation ports. As shown in FIG. 1, the control handle 22 may additionally include buttons 26 for taking pictures with an imaging device on the insertion tube 12, the imaging assembly 14, or both. The proximal end 28 of the control handle 22 may include an accessory outlet 30 (FIG. 1) that provides fluid communication between the air, water and suction channels and the pumps and related accessories. The same outlet 30 or a different outlet can be used for electrical lines to light and imaging components at the distal end of the endoscope 10.

As shown in FIG. 2, the endoscope 10 may further include an imaging device 32 and light sources 34, both of which are disposed at the distal end 36 of the insertion tube 12. The imaging device 32 may include, for example, a lens, single chip sensor, multiple chip sensor or fiber optic implemented devices. The imaging device 32, in electrical communication with a processor and/or monitor, may provide still images or recorded or live video images. The light sources 34 preferably are equidistant from the imaging device 32 to provide even illumination. The intensity of each light source 34 can be adjusted to achieve optimum imaging. The circuits for the imaging device 32 and light sources 34 may be incorporated into a printed circuit board (PCB).

Figure 3:
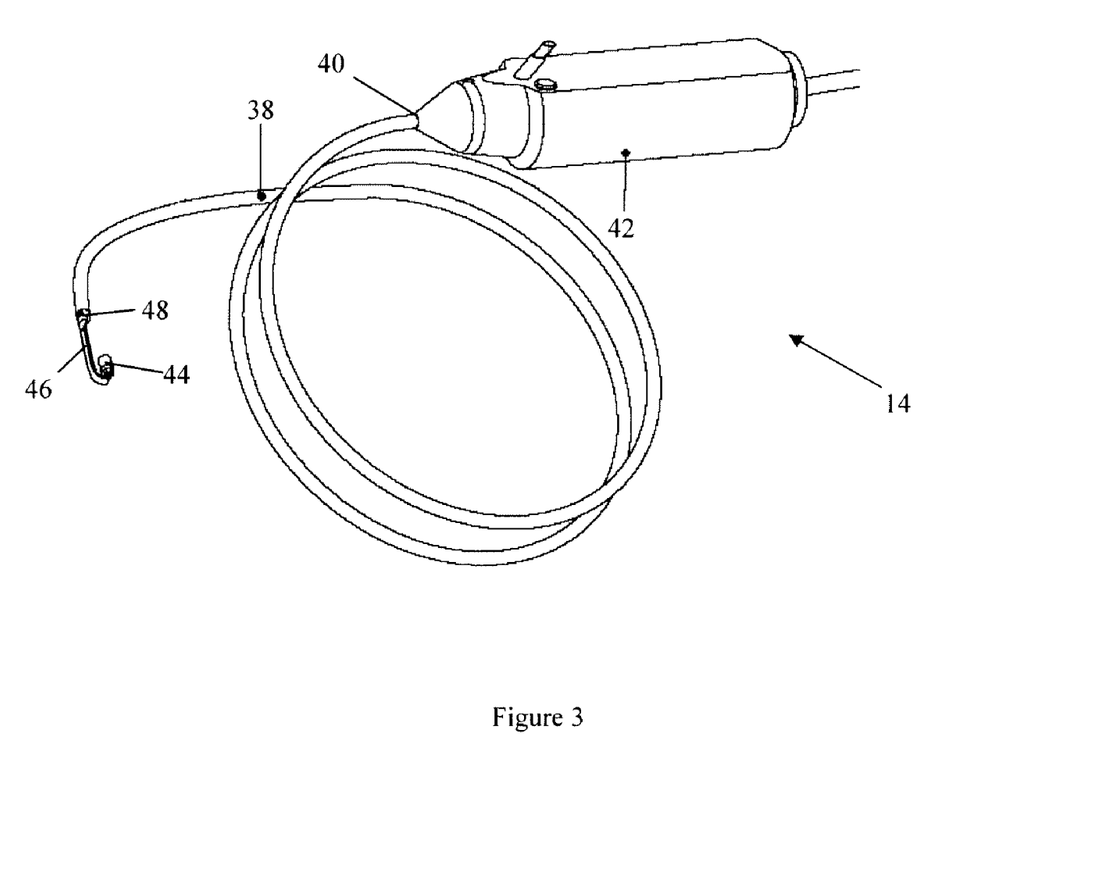
FIG. 3 shows a perspective view of the imaging assembly shown in FIG. 1.
Figure 4:
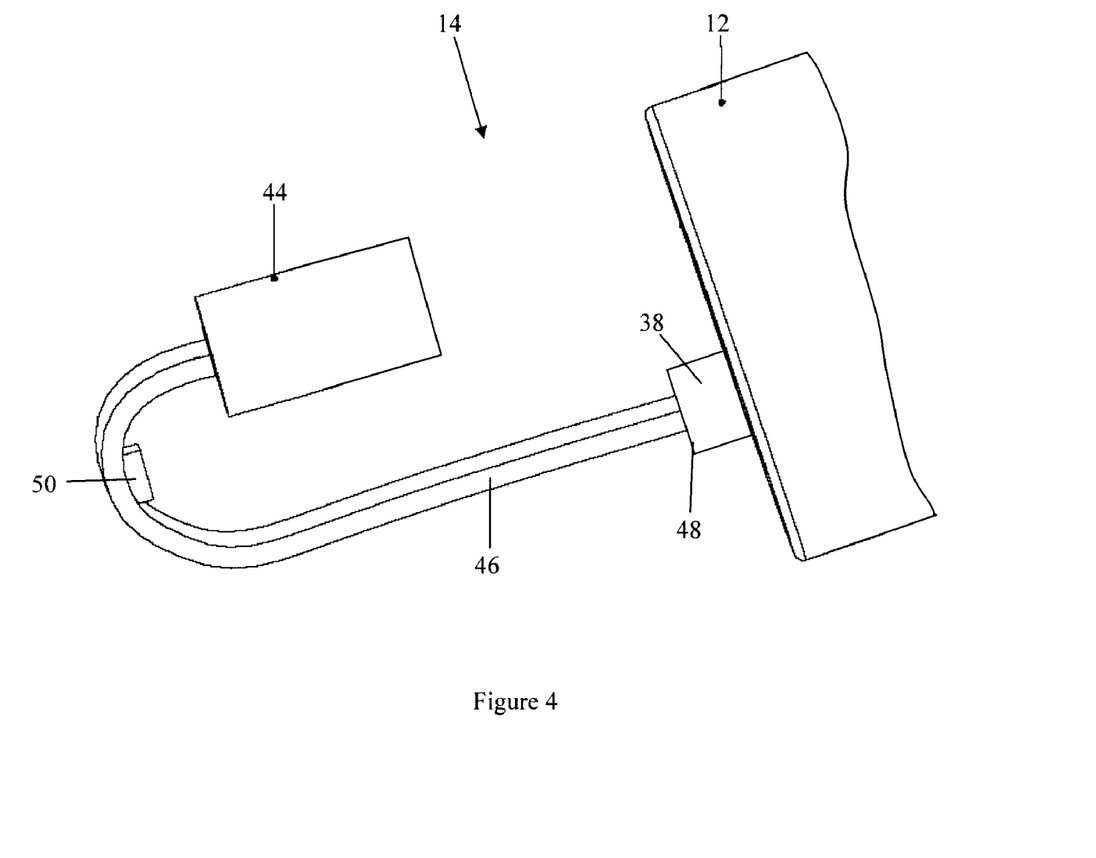
FIG. 4 shows a perspective view of the distal ends of the endoscope and imaging assembly of FIG. 1.

As shown in FIGS. 3 and 4, the imaging assembly 14 may include a tubular body 38, a handle 42 connected to the proximal end 40 of the tubular body 38, an auxiliary imaging device 44, a link 46 that provides physical and/or electrical connection between the auxiliary imaging device 44 to the distal end 48 of the tubular body 38, and an auxiliary light source 50 (FIG. 4). The auxiliary light source 50 may be an LED device.

As shown in FIG. 4, the imaging assembly 14 of the endoscope 10 is used to provide an auxiliary imaging device at the distal end of the insertion tube 12. To this end, the imaging assembly 14 is placed inside one of the channels 16 of the endoscope's insertion tube 12 with its auxiliary imaging device 44 disposed beyond the distal end 36 of the insertion tube 12. This can be accomplished by first inserting the distal end of the imaging assembly 14 into the insertion tube's channel 16 from the endoscope's handle 18 and then pushing the imaging assembly 14 further into the assembly 14 until the auxiliary imaging device 44 and link 46 of the imaging assembly 14 are positioned outside the distal end 36 of the insertion tube 12 as shown in FIG. 4.

Each of the main and auxiliary imaging devices 32, 44 may be an electronic device which converts light incident on photosensitive semiconductor elements into electrical signals. The imaging sensor may detect either color or black-and-white images. The signals from the imaging sensor can be digitized and used to reproduce an image that is incident on the imaging sensor. Two commonly used types of image sensors are Charge Coupled Devices (CCD) such as a VCC-5774 produced by Sanyo of Osaka, Japan and Complementary Metal Oxide Semiconductor (CMOS) camera chips such as an OVT 6910 produced by OmniVision of Sunnyvale, Calif. Preferably, the main imaging device 32 is a CCD imaging device, and the auxiliary imaging device 44 is a CMOS imaging device.

When the imaging assembly 14 is properly installed in the insertion tube 12, the auxiliary imaging device 44 of the imaging assembly 14 preferably faces backwards towards the main imaging device 32 as illustrated in FIG. 4. The auxiliary imaging device 44 may be oriented so that the auxiliary imaging device 44 and the main imaging device 32 have adjacent or overlapping viewing areas. Alternatively, the auxiliary imaging device 44 may be oriented so that the auxiliary imaging device 44 and the main imaging device 32 simultaneously provide different views of the same area. Preferably, the auxiliary imaging device 44 provides a retrograde view of the area, while the main imaging device 32 provides a front view of the area. However, the auxiliary imaging device 44 could be oriented in other directions to provide other views, including views that are substantially parallel to the axis of the main imaging device 32.

As shown in FIG. 4, the link 46 connects the auxiliary imaging device 44 to the distal end 48 of the tubular body 38. Preferably, the link 46 is a flexible link that is at least partially made from a flexible shape memory material that substantially tends to return to its original shape after deformation. Shape memory materials are well known and include shape memory alloys and shape memory polymers. A suitable flexible shape memory material is a shape memory alloy such as nitinol. The flexible link 46 is straightened to allow the distal end of the imaging assembly 14 to be inserted into the proximal end of assembly 14 of the insertion tube 12 and then pushed towards the distal end 36 of the insertion tube 12. When the auxiliary imaging device 44 and flexible link 46 are pushed sufficiently out of the distal end 36 of the insertion tube 12, the flexible link 46 resumes its natural bent configuration as shown in FIG. 3. The natural configuration of the flexible link 46 is the configuration of the flexible link 46 when the flexible link 46 is not subject to any force or stress. When the flexible link 46 resumes its natural bent configuration, the auxiliary imaging device 44 faces substantially back towards the distal end 36 of the insertion tube 12 as shown in FIG. 5.

In the illustrated embodiment, the auxiliary light source 50 of the imaging assembly 14 is placed on the flexible link 46, in particular on the curved concave portion of the flexible link 46. The auxiliary light source 50 provides illumination for the auxiliary imaging device 44 and may face substantially the same direction as the auxiliary imaging device 44 as shown in FIG. 4.

Figure 5:
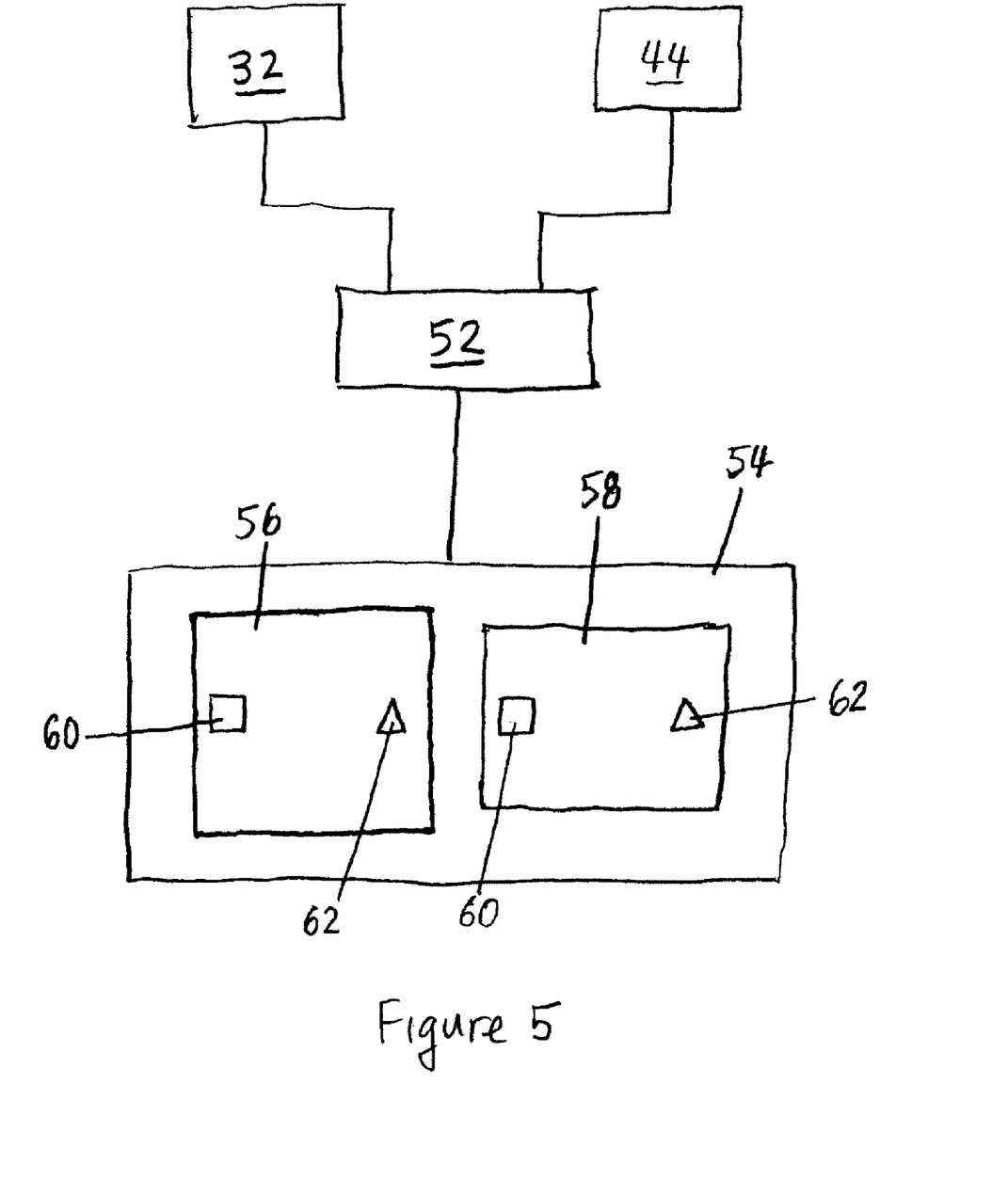
FIG. 5 shows a schematic representation of a display device used with the endoscope of FIG. 1.

The endoscope of the present invention, such as the endoscope 10 shown in FIG. 1, may be part of an endoscope system that may also include a controller 52 and a display device 54, as shown in FIG. 5. In the preferred embodiment shown in FIG. 5, the controller 52 is connected to the main and auxiliary imaging devices 32, 44 to receive image data. The controller 52 may be used to process the image data and transmit the processed image data to the display device 54. The term "controller" as used in this specification is broadly defined. In some embodiments, for example, the controller may simply be a signal processing unit.

In the embodiment shown in FIG. 5, the display device 54 displays, side by side, the image 56 from the main imaging device 32 and the image 58 from the auxiliary imaging device 44. In the present invention, the images may also be displayed on different display devices, and the term "side by side" may simply mean that the two images are positioned so that they can be viewed by the same operator during a medical procedure. The controller 52 preferably incorporates the image data from the main and auxiliary imaging devices 32, 44 into a single signal and sends the signal to the display device 54. In some embodiments, the display device 54 includes a wide screen display with a 16:9 aspect ratio. Preferably, the two images 56, 58 are sized appropriately for display on the wide screen display. For example, the image 56 from the main imaging device 32 may be displayed about 1.5 times larger than the image 58 from the auxiliary imaging device 44. This sizing ratio may also be used to balance the resolution of the two images, as well as to take into account the different aspect ratios of the two images 56, 58. For example, the image 56 from the main imaging device 32 may be displayed with a 1:1 aspect ratio, while the image 58 from the auxiliary imaging device 44 may have a 4:3 aspect ration. The images 56, 58 may also be sized so that the same object, when placed at the same distance from the imaging devices 32, 44, appears to have about the same size in the images 56, 58. The images 56, 58 shown in FIG. 5 are not drawn to scale.

As shown in FIG. 5, one of the images 56, 58 on the display device 54 may be reversed from left for right. With this arrangement, an object 60 that appears on the left side of one image 56 also appears on the left side of the other image 58. Similarly, an object 62 that appears on the right side of one image 56 also appears on the right side of the other image 58, 56. Additionally, when an object moves from the left side of one of the images 56, 58 to the right side, the same object also moves from the left side of the other image 56, 58 to the right side. And, if the object in one image appears to rotated clockwise, the object will appear to rotate clockwise in the other image. Furthermore, the movements of the imaging devices 32, 44 appear to be coordinated. This arrangement makes it easier for an operator to observe, identify and correlate the objects and their movements in both images 56, 58.

Figure 6:
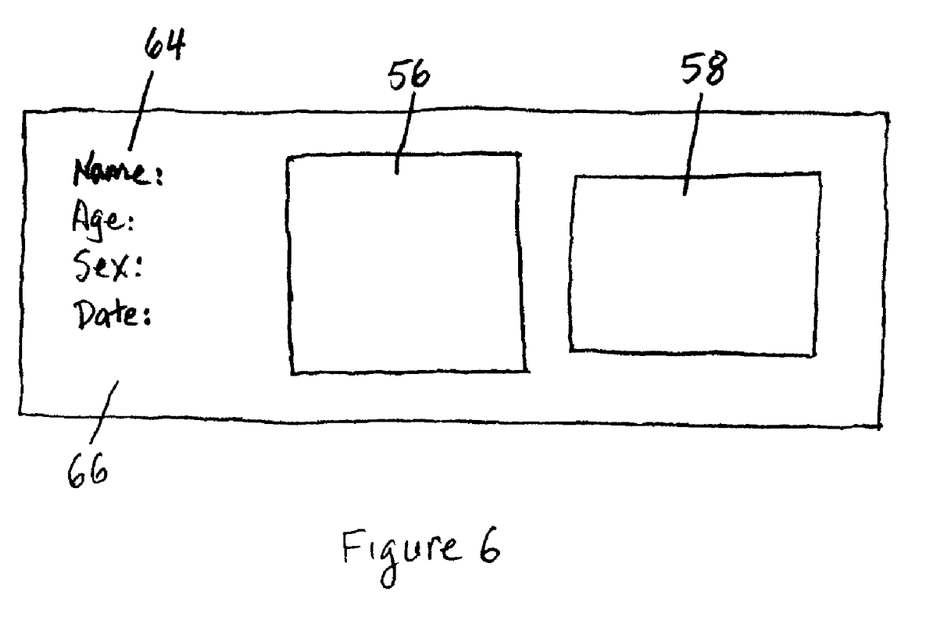
FIG. 6 shows a schematic representation of a screen showing two images and patient information.

Preferably, the data for the two images 56, 58 and possibly other data 64, such as patient information data or a time stamp, are stored in one computer file. In some cases, the patent information may be associated with one of the two images 56, 58. Preferably, the stored images 56, 58 and possibly other data 64 are time-correlated (i.e., they are captured at the same time). For example, as shown in FIG. 6, the two images 56, 58 and possibly other data 64 may be incorporated into one screen 66 in an image file. In some embodiments, the two images 56, 58 and possibly other data 64 may be captured in one jpeg file.

In some preferred embodiments, one or more characteristics of one image 56, 58 may be adjusted to match the same or similar one or more characteristics of the other image 58, 56, so that the images 56, 58 and the objects in the images 56, 58 have similar appearances. The characteristics may include, for example, color, contrast, and brightness. In one example, one or more characteristics of the auxiliary imaging device's image 58 are adjusted to match those of the main imaging device's image 56. Matched images make it easier for an operator to observe, identify and correlate the objects in the images.

In one preferred embodiment, the following technique is used to adjust the characteristics of the auxiliary imaging device's image 58 to match those of the main imaging device's image 56. First, a histogram for each of the RGB colors is created for the auxiliary imaging device's image 58 (called "current file"). The image used to create the histograms may be an average of the past images, such as the past two to ten images, preferably the past four images. And a histogram for each of the RGB colors is created also for the main imaging device's image 56 (called "master file"). This histogram may be the average of the histograms of the past images, such as the histograms of the past two to ten images, preferably the histograms of the past four images.

Second, a minimum and maximum is determined for each histogram by means of thresholding. Then a clip and gain is set for each histogram of the auxiliary imaging device's image to equalize its color gamut to that of the corresponding histogram of the main imaging device's image. In particular, the minimum and maximum for each histogram of the auxiliary imaging device's image are adjusted to match those for the corresponding histogram of the main imaging device's image.

Finally, gamma coefficients are used to adjust the color levels of the histograms of the auxiliary imaging device's image to match those of the histograms of the main imaging device's image. The equations for the gamma coefficients are:

red_gamma_color_balance=
(current_profile.m_AverageRed*Master_average)/(master_profile.m_AverageRed*current_average);

green_gamma_color_balance=
(current_profile.m_AverageGreen*Master_average)/(master_profile.m_AverageGreen*current_average); and blue_gamma_color_balance=
(current_profile.m_AverageBlue*master_average)/(master_profile.m_AverageBlue*current_average)

Gamma coefficients are used because they are simple and convenient and preserve black and white points and because the code can be re-used for conventional gamma correction.

Additional processing of the images, such as sharpening, frame averaging, and noise reduction, may be performed.

The images described above may be still pictures or continuous video images (such as television images). When the images are video images, in the embodiment of the invention in which one or more characteristics of one image are adjusted to match those of another image, the characteristics are adjusted continuously in real time (i.e., dynamically). For example, the characteristics of the video image may be adjusted for every frame of the image. The reason for real time adjustment is that the video images are changing constantly as the lighting, object distance or tissue color varies.

The implementation of the above-described features may be performed digitally by software or firmware in the controller. Alternately, the image manipulation can be performed by hardware image chipsets, FPGAs or other electrical circuitry. These image manipulation techniques are well known in the field of graphic and video processing and will not be described in detail.

Although in the preferred embodiments described above, the images are from the main and auxiliary imaging devices of the same endoscope, the images may also come from imaging devices of different endoscopes such as laparoscopes. For example, when two laparoscopes are used during a procedure, the images from the laparoscopes may have different characteristics due to, for example, different imaging device types, different manufacturing techniques, or differences in lighting sensitivities. The controller that receives images from the laparoscopes may designate any one of the images as a master and then match the second image to the master image. In this way the operator is able to conduct a procedure with consistent visualization across the laparoscopes. Additionally, the present invention may be used with three or more images from two or more endoscopes. For example, two images may be adjusted to match a third image.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

The invention claimed is:

1. A method for matching image characteristics, comprising:
acquiring a first image from a first imaging sensor of an endoscope;
acquiring a second image from a second imaging sensor, wherein the second imaging sensor faces the first imaging sensor; and
using a controller that has been pre-programmed with an algorithm to dynamically adjust images in real-time to adjust at least one characteristic of the second image to match at least one corresponding characteristic of the first image.

2. The method of claim 1, wherein the characteristic is color.

3. The method of claim 1, wherein the characteristic is contrast.

4. The method of claim 1, wherein the characteristic is brightness.

5. The method of claim 1, wherein the at least one characteristic includes first and second characteristics.

6. The method of claim 5, wherein the first and second characteristics are color and contrast.

7. The method of claim 5, wherein the first and second characteristics are color and brightness.

8. The method of claim 5, wherein the first and second characteristics are contrast and brightness.

9. The method of claim 5, wherein the at least one characteristic includes first, second and third characteristics.

10. The method of claim 9, wherein the first, second and third characteristics are color, contrast and brightness.

11. The method of claim 1, wherein the adjustment is performed continuously in real time.

12. The method of claim 1, wherein the algorithm includes:
creating a histogram for each of RGB colors for the first image and a histogram for each of the RGB colors for the second image;
adjusting the gamut of each histogram of the second image to match the gamut of the corresponding histogram of the first image; and
using gamma coefficients to adjust a color level of each histogram of the second image to match a color level of the corresponding histogram of the first image.

13. An endoscopic system comprising:
a first imaging sensor of an endoscope;
a second imaging sensor, wherein the second imaging sensor faces the first imaging sensor; and a controller that has been pre-programmed with an algorithm to dynamically adjust, in real-time, at least one characteristic of an image from the second imaging sensor to match at least one corresponding characteristic of an image from the first imaging sensor of the endoscope.

14. The system of claim 13, wherein the characteristic is color.

15. The system of claim 13, wherein the characteristic is contrast.

16. The system of claim 13, wherein the characteristic is brightness.

17. The system of claim 13, wherein the at least one characteristic includes first and second characteristics.

18. The system of claim 17, wherein the first and second characteristics are color and contrast.

19. The method of claim 17, wherein the first and second characteristics are color and brightness.

20. The system of claim 17, wherein the first and second characteristics are contrast and brightness.

21. The system of claim 17, wherein the at least one characteristic includes first, second and third characteristics.

22. The system of claim 21, wherein the first, second and third characteristics are color, contrast and brightness.

23. The system of claim 13, wherein the controller algorithm includes:
creating histogram for each of RGB colors for the image from the first imaging sensor and a histogram for each of the RGB colors for the image from the second imaging sensor;
adjusting the gamut of each histogram of the image from the second imaging sensor to match the gamut of the corresponding histogram of the image from the first imaging sensor; and
using gamma coefficients to adjust a color level of each histogram of the image from the second imaging sensor to match a color level of the corresponding histogram of the image from the first imaging sensor.

* * * * *